United States Patent [19]

Lotti et al.

[11] 4,215,110
[45] Jul. 29, 1980

[54] METHOD OF TREATING HYPERTENSION

[75] Inventors: Victor J. Lotti, Royat, France; Clement A. Stone, Blue Bell, Pa.

[73] Assignee: Merck & Co., Inc., Rahway, N.J.

[21] Appl. No.: 944,956

[22] Filed: Sep. 22, 1978

Related U.S. Application Data

[63] Continuation of Ser. No. 822,127, Aug. 5, 1977, abandoned, which is a continuation-in-part of Ser. No. 739,685, Nov. 8, 1976, abandoned.

[51] Int. Cl.² ............................................. A61K 37/00
[52] U.S. Cl. .................................................... 424/177
[58] Field of Search ................................ 424/177, 267

[56] References Cited

U.S. PATENT DOCUMENTS

| | | | |
|---|---|---|---|
| 3,268,502 | 8/1966 | Lubke et al. | 424/177 X |
| 3,704,288 | 11/1972 | Skorcz | 424/177 X |
| 3,915,948 | 10/1975 | Wille | 424/177 X |
| 3,929,756 | 12/1975 | Leeman et al. | 424/177 X |
| 3,931,139 | 1/1976 | Wissmann et al. | 424/177 X |
| 3,959,248 | 5/1976 | Veber et al. | 424/177 X |
| 4,013,791 | 3/1977 | Wissmann et al. | 424/177 X |

FOREIGN PATENT DOCUMENTS

| | | | |
|---|---|---|---|
| 832783 | 2/1976 | Belgium | 424/177 |
| 754724 | 7/1975 | South Africa | 424/177 |

OTHER PUBLICATIONS

Science, vol. 178, 10/72 pp. 417 & 418.
Monahan et al., "Chemistry and Biology of Peptides", Proceedings of Third American Peptide Symposium, pp. 602–603, Ann Arbor Pub. Inc., Ann Arbor, Mich., (1972).

*Primary Examiner*—Frederick E. Waddell
*Attorney, Agent, or Firm*—Daniel T. Szura; Harry E. Westlake, Jr.

[57] ABSTRACT

A method of treating hypertension by administration, to hypertensive patients, of an anti-hypertensive amount of certain tripeptides, is disclosed.

11 Claims, No Drawings

METHOD OF TREATING HYPERTENSION

CROSS REFERENCE TO RELATED APPLICATIONS

This is a continuation of application Ser. No. 822,127, filed Aug. 5, 1977, now abandoned, which is a continuation-in-part of application Ser. No. 739,685, filed Nov. 8, 1976, now abandoned.

BACKGROUND OF THE INVENTION

The present invention is concerned with treatment of hypertension using certain tripeptides of the thyrotropin releasing hormone type.

Thyrotropin releasing hormone (TRH) is a known tripeptide, L-pyrogulutamyl-L-histidyl-L-proline-NH$_2$, having thyroid stimulating, antidepressant and lactation promoting activities [U.S. Pat. No. 3,931,139; Science, 178, 417–418 (1972)]. A series of TRH analogs are disclosed in U.S. 3,050,248. These analogs include oxopiperidin-6-ylcarbonyl-histidyl-N-thiazolidinylcarboxamide tripeptides. Other derivatives and analogs of THR are disclosed in "Chemistry and Biology of Peptides", Proceedings of the Third American Peptide Symposium, pages 601–608, Ann Arbor Science Publisher Inc., Ann Arbor, Mich. (1972); Belgian Pat. No. 832,783 and U.S. Pat. No. 3,931,139. There is no suggestion in the prior art of any antihypertensive activity for either TRH or its analogs and derivatives.

It has been discovered that certain of these tripeptides do have antihypertensive activity and may be useful for treating hypertensive patients.

SUMMARY OF THE INVENTION

A method of treating hypertension by administering, to hypertensive patients, of an antihypertensive amount of certain tripeptides.

DESCRIPTION OF PREFERRED EMBODIMENTS

An embodiment of this invention is a method of treating hypertension which comprises administration, to a hypertensive patient, of an antihypertensive amount of a tripeptide, having the formula

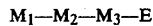

$$M_1-M_2-M_3-E \qquad (1)$$

or a pharmaceutically acceptable salt thereof, wherein
$M_1$ is 2-oxopiperidine-6-carboxylic acid,
$M_2$ is histidine or an $N^{3im}$ R-substituted histidine where R is selected from —CH$_3$ and —CH$_2$—COOH,
$M_3$ is thiazolidine-4-carboxylic acid and
E is selected from —NH$_2$ and —OCH$_3$.

The oral mode of administration is preferred.

Because they contain an asymmetric carbon atom, the individual amino acids of the tripeptides disclosed herein exist as optical isomers. These acid moieties may occur in the tripeptides as the individual isomers, designated as L and D, S and R, − and +, l and d etc.; as racemates (D,L; S,R etc.); or as mixtures of the individual isomers. The S and R designations represent the sinister and rectus absolute spatial configurations of the isomers. Where no isomer designation is given, the amino acid moiety is considered to include all the aforesaid isomers and mixtures.

The salts of the tripeptides disclosed herein encompass all pharmaceutically acceptable salts. There salts include the salts of the tripeptides with inorganic acid e.g. HCl, H$_2$SO$_4$, HBr, H$_3$PO$_4$ and the like as well as with organic acid e.g. cyclohexylcarboxylic acid, fumaric acid, oxalic acid, isethionic acid, tartaric acid, acetic acid, pyroglutamic acid, ascorbic acid, pivalic acid, lactic acid, citric acid, succinic acid, fatty acids e.g. pamoic, palmitic, oleic, stearic, etc., and the like. Pharmaceutically acceptable means that the salts are substantially non-toxic and retain required pharmaceutical activity.

In a more preferred method, the tripeptide has the formula

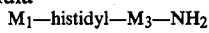

$$M_1-\text{histidyl}-M_3-NH_2 \qquad II$$

A still more preferred method utilizes the tripeptide L-N-(2-oxopiperidin-6-ylcarbonyl)-D,L-histidyl-D,L-N-thiazolidin-4-ylcarboxamide having the formula

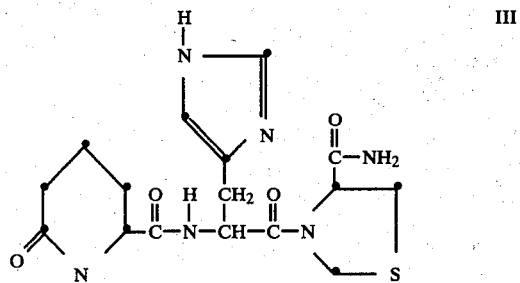

Another embodiment of this invention is a method of treating hypertension which comprises parenteral administration to a hypertensive patient of an anti-hypertensive amount of a tripeptide, having the formula

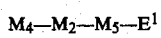

$$M_4-M_2-M_5-E^1 \qquad IV$$

or a pharmaceutically acceptable salt thereof, wherein
$M_4$ is pyroglutamic acid,
$M_2$ is histidine or an $N^{3im}$ R-substituted histidine where R is selected from —CH$_3$ and —CH$_2$—COOH,
$M_5$ is proline, and
$E^1$ is selected from
(a) —NR$_1$R$_2$ wherein R$_1$ and R$_2$ are independently selected from H, C$_3$–C$_8$ alkyl, C$_5$–C$_7$ cycloalkyl, ar—C$_{1-2}$ alkyl and

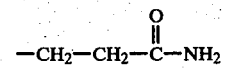

and
(b) —OCH$_3$.

A more preferred embodiment uses a Formula IV peptide where $M_2$ is L-histidine.

In an especially preferred embodiment, each of the amino acid moieties in Formula IV has the L-isomer configuration.

In a most preferred embodiment, the Formula IV peptide is TRH, that is L-pyroglutamyl-L-histidyl-L-proline-amide having the formula

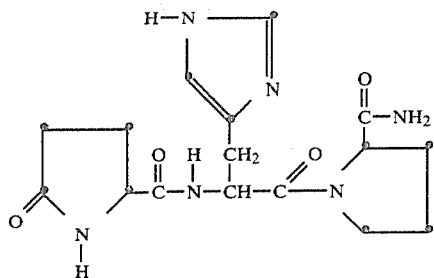

The present tripeptides have antihypertensive activity. This antihypertensive activity was determined using a test procedure which involved administration of representative compounds to spontaneously hypertensive (SH) rats. Using this procedure, the tripeptide L-N(2-oxopiperdin-6-ylcarbonyl)-D,L-histidyl-D,L-N-thiazolidin-4-ylcarboxamide was found to have significant antihypertensive activity when administered orally or intraperitoneally—while the tripeptide, TRH, exhibited significant antihypertensive activity when administered intraperitoneally.

These test results indicate that the present tripeptides are useful to treat hypertension in humans. Hypertension is commonly referred to as "high blood pressure". Thus, the present peptides will effectively reduce blood pressure in hypertensive patients i.e. those having "high blood pressure".

The present tripeptides can be administered to the hypertensive patient in any suitable manner shown to be effective. Thus, they may be administered orally sublingually, subcutaneously, parenterally, i.e. intravenously, intraperitoneally, intramuscularly, etc., by insufflation and the like.

The tripeptides may be administered alone or suitably formulated in combination with other pharmaceutically acceptable compounding ingredients. For oral administration examples of suitable dosage forms are tablets, capsules, liquid formulations such as emulsions, elixirs, solutions, dispersions and the like. For parenteral administration, the dosage form is generally a liquid formulation such as a solution, an emulsion and the like. It may also be advantageous to treat the patient with the peptide by means of a device or carrier system which will continuously or intermittently deliver a measured amount of the peptide for a fixed period of time. This device or carrier system can be appropriately administered for example by attachment, by implant, by ingestion etc.

Dosage levels of the peptide should be adequate to produce the desired antihypertensive effect on the patient. Accordingly the dosage may be varied over a wide range. Daily dosages may range from about 0.03 to about 80 mg/kg of body weight, and preferably from about 0.1 to about 40 mg/kg.

Following are examples of representative dosage formulations.

| Tablet Formulation | |
|---|---|
| Ingredients | Amount (mg) |
| Formula III tripeptide | 25 |
| Calcium phosphate | 120 |
| Lactose | 50 |
| Starch | 23 |
| Magnesium stearate | 1 |
| Injectable Solution | |

| -continued | |
|---|---|
| Ingredients | Amount (mg) |
| TRH | 1 |
| Sodium chloride | 9 |
| Distilled water q.s → 1.0 ml | |
| ml | |

Claims to the invention follow.

What is claimed is:

1. A method of treating hypertension which comprises administration, to a hypertensive patient, of an antihypertensive amount of a tripeptide, having the formula:

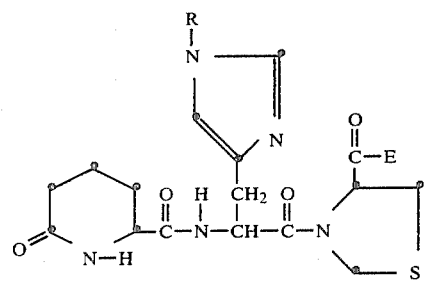

wherein
R is selected from H, —CH₃ and —CH₂—COOH; and
E is —NH₂ and —OCH₃ or a pharmaceutically acceptable salt thereof.

2. The method of claim 1 wherein said tripeptide is designated N-(2-oxopiperidin-6-ylcarbonyl)-histidyl-N-thiazolidin-4-ylcarboxamide having the formula:

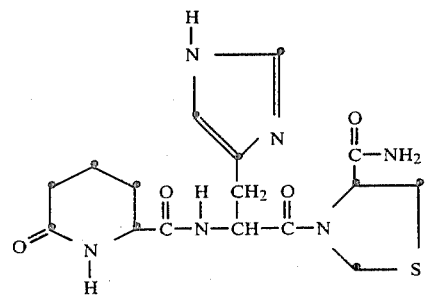

3. The method of claim 2 wherein said tripeptide is designated L-N-(2-oxopiperidin-6-ylcarbonyl)-L-histidyl-L-N-thiazolidin-4-ylcarboxamide.

4. The method of claim 2 wherein said tripeptide is designated L-N-(2-oxopiperidin-6-ylcarbonyl)-D,L-histidyl-D,L-N-thiazolidin-4-ylcarboxamide.

5. The method of claim 1 wherein said administration is oral.

6. The method of claim 4 wherein said administration is oral.

7. A method of treating hypertension which comprises parenteral administration to a hypertensive patient of an antihypertensive amount of a substituted pyroglutamyl-histidyl-prolyl tripeptide, having the formula:

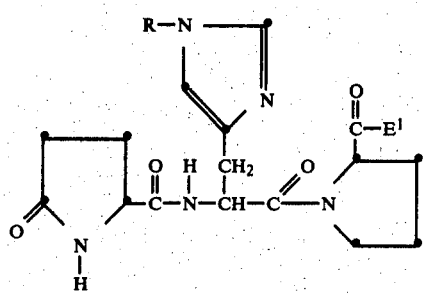

wherein

R is selected from H, —CH$_3$ and —CH$_2$—COOH;

and

E$^1$ is selected from (a) —NR$_1$R$_2$ wherein R$_1$ and R$_2$ are independently selected from H, C$_3$-C$_8$ alkyl, C$_5$-C$_7$ cycloalkyl, ar-C$_{1-2}$-alkyl and

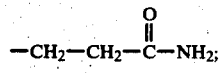

and (b) —OCH$_3$.

8. The method of claim 7 wherein E$^1$ is —NH$_2$.

9. The method of claim 7 wherein said histidyl has the L-configuration having the structure:

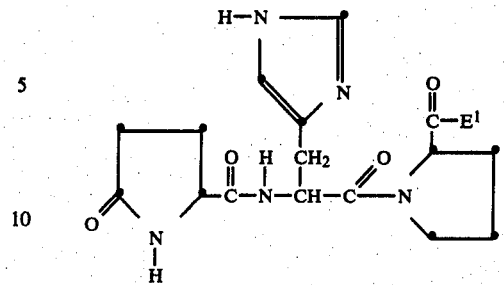

wherein

E$^1$ is selected from (a) —NR$_1$R$_2$ wherein R$_1$ and R$_2$ are independently selected from H, C$_3$-C$_8$ alkyl, C$_5$-C$_7$ cycloalkyl, ar-C$_{1-2}$ alkyl and

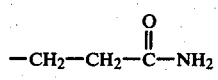

and (b) —OCH$_3$.

10. The method of claim 9 wherein said pyroglutamyl and prolyl each have the L-configuration.

11. The method of claim 10 wherein E$^1$ is —NH$_2$ having the structure:

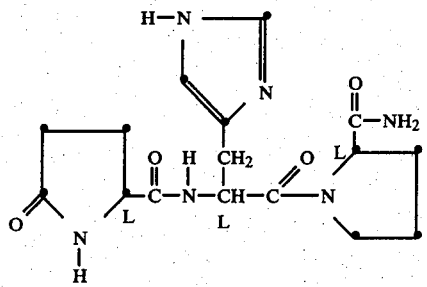

* * * * *